United States Patent [19]

Schröder et al.

[11] Patent Number: 4,772,116
[45] Date of Patent: Sep. 20, 1988

[54] DEVICE FOR THE INTEGRATION OF OPERATING LIGHT IN AN OCULAR EXAMINATION INSTRUMENT

[75] Inventors: Eckhard Schröder, Eckental; Karl-Heinz Wilms, Emmering, both of Fed. Rep. of Germany

[73] Assignees: Meditec Reinhardt Thyzel GmbH, Heroldsberg; Optische Werke G. Rodenstock, Munich, both of Fed. Rep. of Germany

[21] Appl. No.: 122,602

[22] Filed: Nov. 18, 1987

Related U.S. Application Data

[63] Continuation of Ser. No. 732,156, filed as PCT DE84/00179 on Aug. 31, 1984, published as WO85/00966 on Mar. 14, 1985, abandoned.

[30] Foreign Application Priority Data

Aug. 31, 1983 [DE] Fed. Rep. of Germany ....... 3331431

[51] Int. Cl.[4] .............................................. A61B 3/10
[52] U.S. Cl. .................................... 351/214; 351/205; 351/221
[58] Field of Search ............... 351/205, 214, 221, 206; 354/62

[56] References Cited

U.S. PATENT DOCUMENTS 3,982,827 9/1976 Gambs ................................ 351/214
4,461,551 7/1984 Blaha ................................. 351/214

Primary Examiner—Rodney B. Bovernick
Attorney, Agent, or Firm—Barnes & Thornburg

[57] ABSTRACT

A device is described for the integration of operating light and of monitoring and/or target light into an ocular examination instrument, for example a split lamp instrument, whose lamp and monitoring instrument can be rotated through a vertical axis drawn through the eye to be examined.

In the device according to this invention the operating light beam and the monitoring and/or target light beam are directed in a strictly coaxial relationship. The coaxial light beams are first introduced into the axis of the split lamp designed as a concave axis, then deflected by a first optical apparatus out of the revolution axis in an almost vertical direction into the holder of the monitoring instrument and in this holder are deflected almost parallel to the revolution axis and finally integrated into the beam path of the monitoring instruments outside the revolution axis by a third optical apparatus.

28 Claims, 1 Drawing Sheet

DEVICE FOR THE INTEGRATION OF OPERATING LIGHT IN AN OCULAR EXAMINATION INSTRUMENT

This is a continuation of application Ser. No. 732,156, filed as PCT DE84/00179 on Aug. 31, 1984, published as W085/00966 on Mar. 14, 1985, now abandoned.

BACKGROUND AND SUMMARY OF THE INVENTION

The invention relates to a device for the integration of an operating light in an ocular examination instrument.

Such devices are, for example, required for the coagulation of the retina or for photo-surgery on the human eye.

Typically, ocular examination instruments must be able to be rotated through a vertical axis which is drawn through the eye being examined during the examination/treatment process. In addition, the examining instrument should be adjustable in a vertical direction and should be able to be moved by means of a cross-table in the x and y direction.

These adjustment possibilities must be followed by the beam path of the integrated operating laser beam. A device for the integration of the operating light which does not interfere with the adjustability of the ocular examination instrument is known, for example, from the German utility model No. 7 225 429. In this utility model it is proposed that a slit lamp be modified in such a way that the beam of an operating or coagulating laser is directed on to the human eye through the slit lamp. For this purpose, the operating light beam is first introduced into the axis of rotation of the slit lamp which is designed as a hollow shaft, the operating light beam is deflected out of the axis of rotation by means of a mirror above the sweep arm of the slit lamp and by means of a second mirror is introduced into the beam path of the slit lamp. The operating light beam then enters the normal beam path system of the slit lamp through a bored mirror and runs parallel to the illuminating light of the slit lamp behind this bored mirror.

This known device has a number of disadvantages:

To integrate the operating light beam, it is necessary to make adjustments to the beam path system of the slit lamp which have a considerable effect on its functioning. Despite these adjustments, the beam path system of the slit lamp limits the aperture of the laser beam to very small values.

Furthermore, as a result of the many optical surfaces the operating light beam passes through in the slit lamp "ghost pictures" and reflections of the operating light beam may occur. This may also have the effect that part of the operating light enters the eye of the patient in an incorrect way and causes unintentional damage there.

In addition, the operating light is also partially guided without any casing in the area between the axis of rotation and the split lamp.

Also, in the known device only the light of an operating laser is integrated in the beam path of an ocular examination instrument. However, when for example, a neodymium YAG laser, which operates in the infra-red range, is used as the operating light source, it would be advantageous if additionally a "target laser" whose light is in the visible spectral range were used as an observation light source or as a target light source.

As the operating light beam is directed via the slit lamp in the known device, the operating light beam and the observation beam path can never be coincident when advantage is taken of the fact that the slit lamp can be rotated independently of the observation instrument. However, as it is necessary in many applications for the operating light beam and the observation beam path to be coincident, the free rotation function of the slit lamp with regard to the observation area can, for this reason, and as has been recognised according to this invnention, not be made use of in the known device.

A device of another kind, in which the light of an operating laser is introduced into the beam path of an ocular examination instrument by a mirror, is known from U.S. Pat. No. 3,769,963. With this device, the light of the operating laser is introduced by a mirror into the beam path between the eye under examination and the observation instrument, while the light of the illumination laser is led to the eye by a light conductor. In addition, the light of the illumination laser can be introduced into the beam path of the operating laser by a mirror in such a way that the light beam of the illumination laser can also be used as a target light beam.

This known device of another kind has, however, the disadvantage that—to ensure that the ocular examination instrument can be vertically adjusted and rotated within the usual limits—the light of the laser has to be led over long stretches by a flexible glass fiber conductor. Such glass fiber conductors are, however, particularly prone to disturbance for light in the infra-red range. Furthermore, this proneness to disturbance is increased if their flexibility is subjected to a lot of strain so that, where possible, the use of such flexible light conductors should not be considered, particularly for lasers which operate in the infra-red range.

The object of this invention is to provide a device for the integration of operating light in a rotatable and adjustable ocular examination instrument, whereby operating light beam and, if required, also an observation and/or target light laser can be integrated in the beam path of the observation instrument without interfering with the adjustability or rotatability and without the use of flexible light conductors or disturbing articulated optical systems and without interfering with the optical system of the ocular examination instrument.

The underlying problems are solved according to the present invention in that a first optical device deflects the coaxial light beams into the pivot arm of the observation apparatus, in that a second and a third optical device are attached in or on the pivot arm, in that the second optical device deflects the light beams parallel to the axis of rotation of the instrument, in that the third optical device integrates the light beams into the beam path of the observation apparatus and in that, if additional observation and/or target beams are to be integrated, the light beams of the observation and/or target source are conducted coaxially to the operating light beam.

According to this invention the operating light beam and, where required, the observation and/or target light beams directed coaxially to the operating light beam, are first directed into the axis of rotation of the ocular examination instrument and then integrated in the beam path of the observation instrument outside this revolution axis. In this way, the vertical adjustability and the rotatability of the ocular examination instrument remain unaffected. By diverting the coaxial light beams into the sweep arm of the observation instrument, there is no need to make any adjustments to the optical structure, for example, of the slit lamp.

In this way, the device according to this invention has the advantage that the coaxial beams are guided completely within parts of the mounting of the ocular examination instrument and that the beam path is completely encapsulated without any additional construction effort.

In this context coaxial beam guidance means a beam guidance in which the axes of the individual laser beams coincide; as a non-essential requirement one of the laser beams should have a ring-shaped cross-section.

According to another feature of this invention, a large aperture can be attained which is required for small spot sizes of the operating light beam in the order of 10 µm.

The expanding optical system of this invention may consist of two optical elements, where one has a negative and the other a positive refractive power. The optical elements can thereby be single lenses or several lenses.

The rotatability of the third optical element according to this invention allows the integration of the beam path of other devices, for example of an photographic device, into the beam path of the ocular examination instrument so that the device according to this invention, can be used universally.

Moreover, ghost pictures, reflections, etc. resulting from the mirror-effects etc. are effectively suppressed in the arrangement according to this invention.

The fixed arrangement of the light sources according to this invention is of particular advantage when, for example, the light sources, and in particular the lasers, are large and heavy and thus cannot be attached to the ocular examination instrument itself.

The device according to this invention can be used in conjunction with the most varied ocular examination instruments, for example in conjunction with a slit lamp instrument or with an ophthalmoscope.

BRIEF DESCRIPTION OF THE DRAWINGS

These and other objects, features and advantages of the present invention will become more apparent from the following description when taken in connection with the accompanying drawing which shows, for purposes of illustration only, one embodiment in accordance with the present invention, and wherein:

The single FIGURE is a schematic view of an ocular examination instrument in accordance with the present invention.

DETAILED DESCRIPTION OF THE DRAWINGS

Method of Carrying Out the Invention

Figure 1:
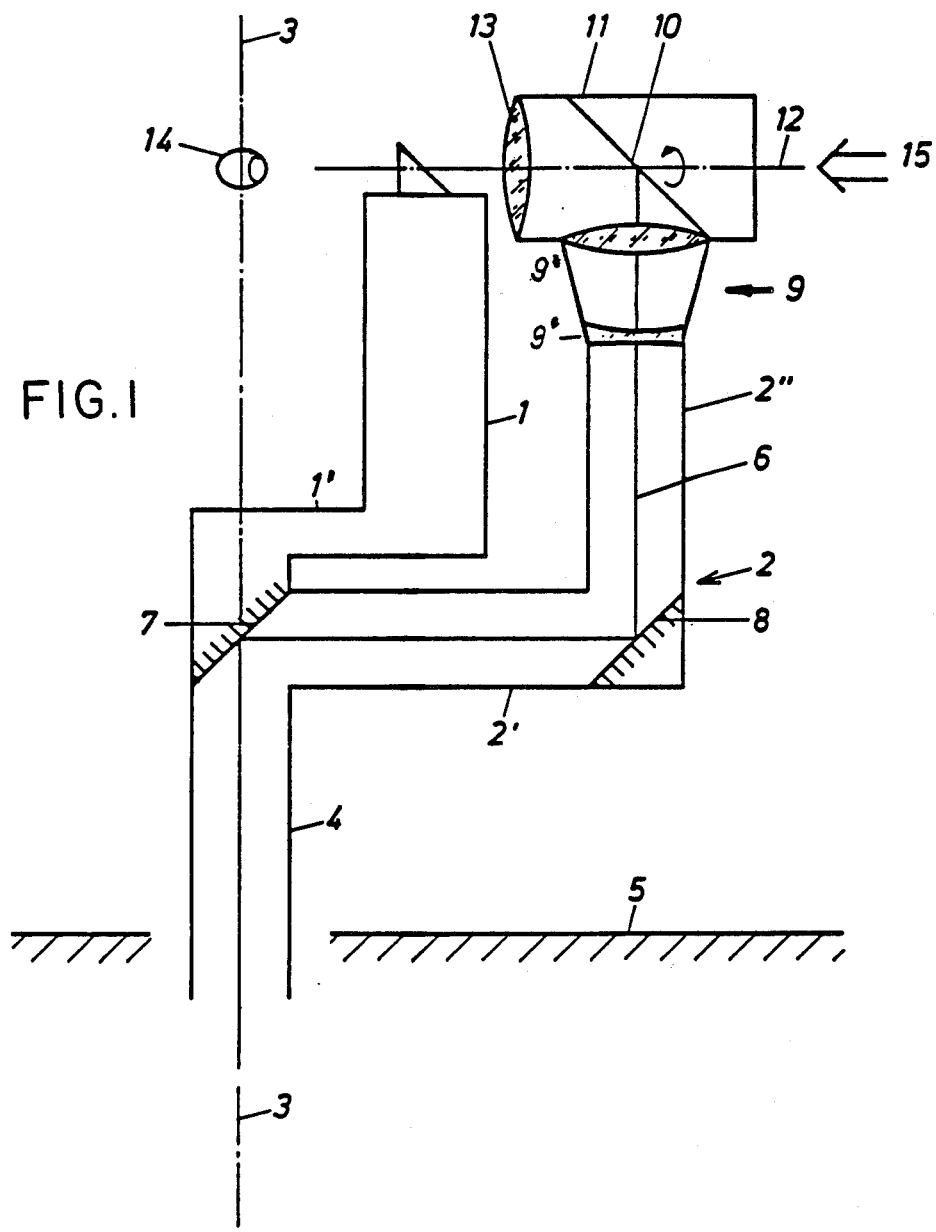

A slit lamp 1, shown only schematically, is rotatable by means of a sweep arm 1' about an axis of rotation 3 over an angle range of approximately ±80°. To a holder or mounting 4, to which the sweep arm 1' of the slit lamp 1 is connected, there is also fixed a sweep arm 2, on which a stereo microscope 15, is not further represented, is fixed as a observation instrument.

The holder or mounting 4 and therewith the slit lamp 1 and the stereo microscope 15 are with regard to a table 5 adjustable in a vertical direction and can also be moved by means of a cross-table, not further represented, in the x and the y direction.

The holder or mounting 4 and the sweep arm 2 are hollow so that a light beam 6 can be guided within the same, where said light beam 6 is for example introduced at the end of the holder or mounting 4 by means of a mirror or prism, which is not further represented. The light beam 6 introduced into holder 4 is first directed coaxially to the axis of rotation 3 and then deflected into the horizontal part 2' of the sweep arm 2 by a deflection mirror 7. A deflection mirror 8 deflects the light beam 6 into the vertical part 2" of the sweep arm 2. The deflected light beam is expanded by an optical expansion system 9, for example from a diameter of 6 mm to a diameter of 30 mm. Subsequently, the light beam 6 is deflected by a deflection mirror 10 in a housing 11, fixed on the top end of the vertical part 2' of the sweep arm 2, into the optical axis 12 of the observation instrument. The expanded beam is focussed on or in the eye to be examined 14 by a focussing lens 13 which is part of the observation instrument.

The optical expansion system 9 consists of two optical elements 9' and 9", of which element 9' has a negative and element 9" a positive refractive power. In this arrangement, each element can comprise one or more lenses; the negative element 9' can additionally, for example, be constructed exchangeable by means of a turret-type structure.

The deflection mirror 10 can be rotated through 360° around the optical axis 12. In this way, it is possible to integrate other optical instruments, which are fixed to the sides or to the surface of housing 11 and which have their own beam path, into the beam path of the observation instrument. An example for such an additional instrument to be integrated is, for example, a smaller light source or a photographic option.

As the observation takes place, for example, by means of the split lamp microscope through the partially transmitting mirror 10, reflections on the elements of the focussing lens 13 can result in ghost pictures.

To avoid such ghost pictures, different parts of the deflection mirror 10 are used for the target beam of the helium-neon laser and the operating beam. This area separation can be achieved in particular by providing that those areas of the deflection mirror through which the observation takes place from the rear of housing 11, have a reflection factor for the wavelength of the target beam which is as low as possible, while the total mirror surface has a reflection factor of almost 100% for the wavelength of the operating beam.

Furthermore, it is also of advantage if the surfaces of the mentioned optical system which produce ghost pictures are provided with an anti-reflection coating.

While we have shown and described only one embodiment in accordance with the present invention, it is understood that the same is not limited thereto but is susceptible of numerous changes and modifications as known to those skilled in the art, and we therefore do not wish to be limited to the details shown and described herein but intend to cover all such changes and modifications as are encompassed by the scope of the appended claims.

We claim:

1. An arrangement for integrating an operating light into an eye examination apparatus which includes observation means having a beam path and means producing an illuminating light which are each pivotal about an axis of rotation passing substantially through the eye to be examined, comprising means for initially directing a light beam means of the operating light substantially in the axis of rotation, first optical means for deflecting the operating light beam means approximately perpendicularly out of the axis of rotation, second optical means for deflecting the operating light beam means approximately parallel to said axis of rotation, third optical means for deflecting the operating light beam means onto the eye to be examined, said observation means including pivot arm means, the first optical means being operable to deflect the operating light beam means into the pivot arm means and the second and third optical means being operatively connected with said pivot arm means, and the third optical means being operable to integrate the light beam means into the beam path of the observation means so that the free pivotability of the eye examination apparatus is not impaired.

2. An arrangement according to claim 1, in which further light source means including at least one of observation and target light source are provided whose light beam means are to be integrated, and in which the light beam means of the further light source means are guided substantially coaxially to the operating light beam means.

3. An arrangement according to claim 1, wherein the eye examination apparatus includes a slit lamp means as further light source means.

4. An arrangement according to claim 1, further comprising expanding optical means arranged ahead of the third optical means operable to expand the concentric light beam means and focusing means arranged after the third optical means operable to focus the expanded light beam means into the eye to be examined or treated.

5. An arrangement according to claim 4, wherein the expanding optical means includes an element having a negative refractive power and an element having a positive refractive power.

6. An arrangement according to claim 4, wherein the third optical means is rotatable through at least 90° for integrating the beam path of other devices forming part of the apparatus into the beam path of the observation means.

7. An arrangement according to claim 6, wherein said third optical means is rotatable through 360°.

8. An arrangement according to claim 6, wherein the first, second and third optical means are one of deflection mirrors or deflection prisms.

9. An arrangement according to claim 6, wherein separate areas on the third optical means serve for the deflection of the observation and/or target light as well as of the operating light.

10. An arrangement according to claim 9, wherein the separation is achieved in that the area through which takes place the observation, has a relatively low degree of reflection for the wavelength of a target light and a relatively high degree of reflection for the operating light.

11. An arrangement according to claim 10, wherein the entire surface of the third optical means has a reflection factor of nearly 100° for the wavelength of the operating light.

12. An arrangement with objective means according to claim 9, wherein only those optical surfaces of the objective means of the apparatus are coated with an anti-reflection coating which cause disturbing reflections of the observation, respectively, target light.

13. An arrangement according to claim 12, wherein the target light source is a helium neon laser and the operating light source a neodym-YAG-laser.

14. An arrangement according to claim 1, wherein the eye examination apparatus is a slit lamp apparatus.

15. An arrangement according to claim 1, wherein the eye examination apparatus is an ophthalmoscope.

16. An arrangement according to claim 1, wherein the third optical means is rotatable through at least 90° for integrating the beam path of other devices forming part of the apparatus into the beam path of the observation means.

17. An arrangement according to claim 1, wherein the first, second and third optical means are one of deflection mirrors or deflection prisms.

18. An arrangement according to claim 1, wherein separate areas on the third optical means serve for the deflection of the observation and/or target light as well as of the operating light.

19. An arrangement according to claim 18, wherein the separation is achieved in that the area through which takes place the observation, has a relatively low degree of reflection for the wavelength of a target light and a relatively high degree of reflection for the operating light.

20. An arrangement with objective means according to claim 1, wherein only those optical surfaces of the objective means of the apparatus are coated with an anti-reflection coating which cause disturbing reflections of the observation, respectively, target light.

21. An arrangement for integrating an operating light into an eye examination apparatus which includes illuminating means for illuminating the eye to be examined and observation means having an observation beam path for viewing the eye to be examined, said illuminating means and said observation means being each pivotal about an axis essentially passing through the eye to be examined, means for guiding a light beam means of the operating light substantially in the direction of said axis, first optical means for deflecting said light beam means into said pivot arm means, second and third optical means operatively connected with said pivot arm means, said second optical means being operable to deflect said light beam means substantially parallel to said axis, and said third optical means being operable to integrate the light beam means into the beam path of the observation means.

22. An arrangement according to claim 21, wherein the optical axis of the observation beam path and the optical axis of the operating light beam path coincide over part of their respective paths.

23. An arrangement with further means producing at least one of observation light and target light beam means according to claim 21, wherein the light beam means of the operating light and of the observation and/or target light are guided by said guide and optical means substantially coaxially with respect to each other.

24. An arrangement for an eye examination apparatus which includes means enabling adjustment thereof in the x-y directions according to claim 21, wherein said illuminating means is pivotal about said axis.

25. An arrangement according to claim 24, wherein said illuminating means provides an illuminating light beam means which passes through said third optical means.

26. An arrangement according to claim 25, wherein said illuminating light beam means is substantially coaxial to said operating light beam means over at least part of the travel toward the eye to be examined.

27. An arrangement according to claim 26, wherein said illuminating means is a slit lamp.

28. An arrangement according to claim 21, wherein said illuminating means is a slit lamp.

* * * * *